United States Patent [19]

Dryden, Jr et al.

[11] Patent Number: 4,555,362

[45] Date of Patent: Nov. 26, 1985

[54] METHOD AND INTERMEDIATES FOR PRODUCING α-L-ASPARTYL-L-PHENYLALANINE

[75] Inventors: Hugh L. Dryden, Jr, Deerfield; John B. Hill, Woodstock, both of Ill.

[73] Assignee: G. D. Searle & Co., Skokie, Ill.

[21] Appl. No.: 610,376

[22] Filed: May 15, 1984

Related U.S. Application Data

[60] Continuation-in-part of Ser. No. 580,912, Feb. 16, 1984, which is a division of Ser. No. 506,465, Jun. 20, 1983, Pat. No. 4,440,677.

[51] Int. Cl.$^4$ ............................................. C07C 103/52
[52] U.S. Cl. ............................................. 260/112.5 R
[58] Field of Search ................................. 260/112.5 R

[56] References Cited

U.S. PATENT DOCUMENTS

| | | | |
|---|---|---|---|
| 3,879,372 | 4/1975 | Boesten | 260/112.5 R |
| 4,440,667 | 4/1984 | Dryden et al. | 260/112.5 R |
| 4,480,112 | 10/1984 | Dryden et al. | 260/112.5 R |

FOREIGN PATENT DOCUMENTS 0058063  8/1982  European Pat. Off. .
2098220 11/1982  United Kingdom .

OTHER PUBLICATIONS

*Chemical Abstracts*, vol. 64, 1966, Abst. No. 19754C.

*Primary Examiner*—Delbert R. Phillips
*Assistant Examiner*—F. T. Moezie
*Attorney, Agent, or Firm*—Steven M. Odre; John J. McDonnell

[57] ABSTRACT

This invention encompasses a method and intermediates for preparing a commercial sweetening agent, α-L-aspartyl-L-phenylalanine methyl ester. The process involves reacting L-aspartic acid with diketene to form N-acetoacetyl-L-aspartic acid which is converted to N-acetoacetyl-L-aspartic anhydride by reaction with acetic anhydride. N-acetoacetyl-L-aspartic anhydride is reacted with L-phenylalanine methyl ester to provide N-acetoacetyl-α-L-aspartyl-L-phenylalanine methyl ester which is converted to α-L-aspartyl-L-phenylalanine methyl ester by reaction with hydroxylamine hydrochloride.

2 Claims, No Drawings

METHOD AND INTERMEDIATES FOR PRODUCING α-L-ASPARTYL-L-PHENYLALANINE

This application is a continuation-in-part of application Ser. No. 06/580,912 filed Feb. 16, 1984, which is a division of Ser. No. 06/506,465 filed June 20, 1983, now U.S. Pat. No. 4,440,677.

BACKGROUND OF THE INVENTION

α-L-aspartyl-L-phenylalanine methyl ester is a sweetening agent which is about 200 times sweeter than sucrose. The compound and its uses are extensively taught in U.S. Pat. Nos. 3,492,131; 3,642.491; and 3,780,189. A variety of methods for the economical synthesis of α-L-aspartyl-L-phenylalanine are known, for example, U.S. Pat. Nos. 3,933,781 and 4,173,562 describe the use of N-protected-L-aspartic anhydride in preparing α-L-aspartyl-L-phenylalanine methyl ester.

Chem Abstracts 64 19754C (1966) describes acetoacetyl derivatives of glycine, alanine, leucine, threonine, methionine and tryptophan made from the reaction of the corresponding amino acid with diketene. The acetoacetyl derivative of leucylglycine methyl ester is described in Tetrahedron Letters 10, 605–608 (1965). J. Chem Soc (C), 350, (1969) describes the preparation of N-acetoacetylvaline and N-acetoacetylvalyvaline from valine and valylvaline respectively and diketene.

BRIEF DESCRIPTION OF THE INVENTION

The present invention involves a high yield large scale synthesis of α-L-aspartyl-L-phenylalanine methyl ester.

The preferred embodiment of the invention is illustrated in Scheme I.

SCHEME 1

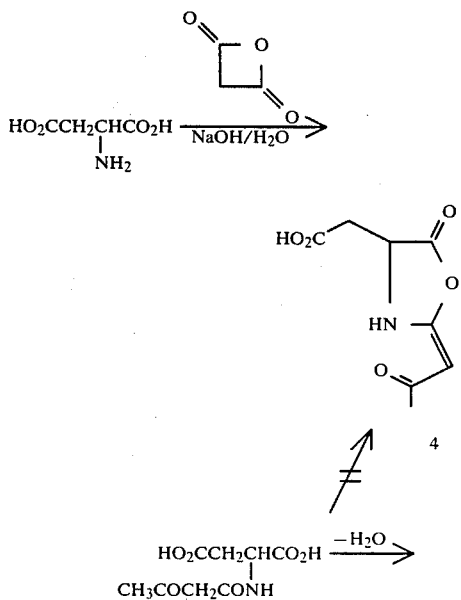

-continued
SCHEME 1

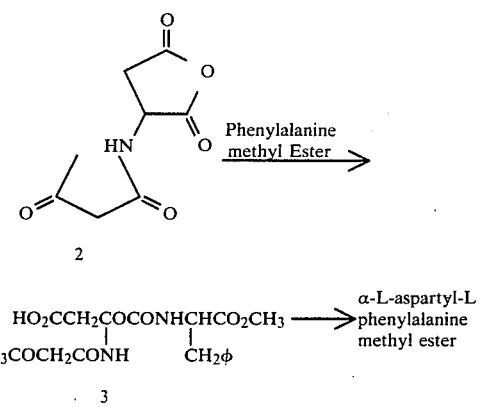

It has been discovered that diketene selectively reacts with the amino group of aspartic acid in high yield even though two carboxylic acid groups are present in aspartic acid. This reaction is conducted in basic solution, preferably basic methanol. The acetoacetyl group is stable during dehydrating procedures which form the anhydride and it is surprising that N-acetoacetyl L-aspartic anhydride is formed instead of the predicted oxazolidinone 4 in Scheme I. Acid anhydrides such as acetic anhydride and propionic acid anhydride and phosphorous trichloride are preferred dehydrating agents for converting N-acetoacetyl L-aspartic acid to N-acetoacetyl L-aspartic anhydride. The acetoacetyl group is removed with hydroxylamine salt such as the hydrochloride or sulfate under mild conditions in 99% yield without disturbing the ester and/or the free carboxyl group—a problem associated with removal of the formyl and acetyl group. For example, the formyl is removed by strong acids in aqueous methanol which causes esterification and hydrolysis.

Thus, the invention encompasses a method for preparing L-aspartyl-L-phenylalanine methyl ester comprising:
  (a) reacting L-aspartic acid with diketene in basic solution at −10° C. to +20° C. to form N-acetoacetyl-L-aspartic acid.
  (b) dehydrating N-acetoacetyl-L-aspartic acid with a dehydrating agent to form N-acetoacetyl-L-aspartic anhydride.
  (c) reacting N-acetoacetyl-L-aspartic anhydride with L-phenylalanine methyl ester to form N-acetoacetyl-α-L-aspartyl-L-phenylalanine methyl ester.
  (d) removing the N-acetoacetyl group from N-acetoacetyl-α-L-aspartyl-L-phenylalanine methyl ester by reaction with an hydrazine salt or an hydroxylamine salt.

The preferable dehydrating agents are acetic anhydride in acetic acid or ethyl acetate or phosphorous trichloride in ethyl acetate/acetic acid.

Novel intermediates of the invention are
N-acetoacetyl-L-aspartic acid
N-acetoacetyl-L-aspartic anhydride
N-acetoacetyl-α-L-aspartyl-L-phenylalanine

DETAILED DESCRIPTION OF THE INVENTION

The above-named novel intermediates are shown in Scheme I as structures 1, 2 and 3, respectively. Free carboxylic acid groups in these compounds can be converted to the respective salts such as sodium, potassium, calcium and the like by reaction with the appropriate base. Thus reaction mixtures which contain compound 1, 2 or 3 whether as the free base or acid or base salts are within the scope of the invention.

EXAMPLE 1

N-acetoacetyl-L-aspartic acid

L-aspartic acid, 13.3. parts, was added to 100 parts by volume of 2N aqueous sodium hydroxide and the resulting solution was cooled to 0°–10° C. in an ice bath. Diketene, 8.4 parts, was added and the resulting two phase mixture was stirred for 2.5 hours at 0°–10° C. The homogeneous solution was washed twice with 100 parts by volume of ether and the aqueous layer was acidified with 16.6 parts by volume of concentrated hydrochloric acid. This solution was extracted three times with 100 parts by volume of ethyl acetate, the combined extracts were dried over sodium sulfate, filtered and the solvent evaporated under vacuum at 25°–30° C. to give 2.3 parts of N-aceto-acetyl-L-aspartic acid, mp 127°–129.5° C.

Elemental analysis for $C_8H_{11}NO_6$:
Calc. C, 44.24; H, 5.10 N, 6.45; Found C, 44.59; H 5.24; N, 6.10.
NMR (DMSO-D6): $\delta$2.18, 3H, s; 2.70, 2H, d; 3.38; 2H, s; 4.59, 1H, m; 8.40, 1H, m.

N-acetoacetyl-L-aspartic anhydride 1.41 parts of N-acetoacetyl-L-aspartic acid were dissolved in 25 parts by volume of acetic acid, and 5 parts by volume of acetic anhydride were added and the mixture was stirred overnight under nitrogen. Solvent was removed under vacuum at 40°–45° C. 50 parts by volume of acetic acid were added and the evaporation repeated to form N-acetoacetyl-L-aspartic anhydride.

N-acetoacetyl-L-aspartyl-L-phenylalanine methyl ester

The crude anhydride was stirred with 20 parts by volume of toluene and 5 parts by volume of acetic acid. 8 parts by volume of an 0.81 Molar solution of L-phenylalanine methyl ester in toluene was added and stirred overnight. The resulting solution was evaporated under vacuum to give an oil. The oil was stirred with 50 parts by volume of ether which resulted in formation of a solid. This solid was isolated by filtration, washed with ether and air dried to give 1.61 parts of N-acetoacetyl-L-aspartyl-L-phenylalanine methyl ester as a mixture of $\alpha$ and $\beta$ isomers.

NMR (DMSO-D6): $\delta$2.13, 3H, s; 2.60, 2H, m; 3.02, 2H, m; 3.35, 2H, s; 3.60, 3H, s; 4.54, 1H, m; 7.25, 5H, s; 8.30, 2H, m.

L-Aspartyl-L-phenylalanine methyl ester 1.41 parts of N-acetoacetyl-L-aspartyl-L-phenylalanine methyl ester was dissolved in 50 parts by volume of 1:1 aqueous acetic acid, 0.259 parts of hydroxylamine hydrochloride was added and the solution stirred at ambient temperatures for 4 hours to provide a mixture of $\alpha$ and $\beta$ isomers of L-aspartyl-L-phenylalanine methyl ester.

EXAMPLE 2

Disodium N-acetoacetylaspartate 8.1 parts of sodium hydroxide were dissolved in 100 parts by volume of water and the solution cooled to 0°–5° C. 13.3 parts of L-aspartic acid were added and stirred until all dissolved, then 15.8 parts by volume of diketene were added dropwise over 90 minutes, stirred at 0°–10° C. for an additional 2.5 hours, and filtered. The homogeneous solution was evaporated to dryness under vacuum at 35°–40° C. Disodium N-acetoacetylaspartate was obtained as a white foam.

N-acetoacetyl-L-aspartyl-L-phenylalanine methyl ester

Crude disodium N-acetoacetylaspartate, 28.51 parts, was stirred with 200 parts by volume of ethyl acetate and 11.7 parts by volume of acetic acid at 0°–5° C. under argon while 4.37 parts by volume of phosphorous trichloride was added dropwise. The resulting mixture was allowed to warm to ambient temperatures while stirring for 20 hours. To the resulting solution which contains N-acetoacetyl-L-aspartic anhydride was added dropwise over a 2 hour period 122 parts by volume of 0.9M L-phenylalanine methyl ester in dioxane. After continued stirring for 20 hours, the solvent was evaporated under vacuum at 35°–40° C. Toluene, 200 parts by volume, was added to the residue and the evaporation was repeated, giving crude N-acetoacetyl-L-aspartyl-L-phenylalanine methyl ester as a semi-solid yellow residue.

L-aspartyl-L-phenylalanine methyl ester hydrochloride dihydrate

The crude N-acetoacetyl-L-aspartyl-L-phenylalanine methyl ester was dissolved in 100 parts by volume of water and 11.7 parts by volume of acetic acid. Toluene, 200 parts by volume, and hydroxylamine hydrochloride, 6.95 parts by volume, were added and the mixture stirred for 2.5 hours. The aqueous layer was separated and cooled to 0°–5° C. 15 parts by volume concentrated hydrochloric acid were added and the resulting mixture was cooled at 0°–5° C. overnight. The precipitate was collected on a filter and air dried for 3 hours to give 26.4 parts of $\alpha$-L-aspartyl-L-phenylalanine methyl ester hydrochloride dihydrate.

$\alpha$-L-aspartyl-L-phenylalanine methyl ester 12.5 parts of $\alpha$-L-aspartyl-L-phenylalanine methyl ester hydrochloride dihydrate was dissolved in 100 parts by volume of water and aqueous sodium carbonate added to pH3, then heated to 60° C. and adjusted to pH4.5. The reaction mixture was cooled to 5° C. for three hours and the precipitate was collected on a filter and dried for 18 hours under vacuum at 60° C. to give 7.6 parts $\alpha$-L-aspartyl-L-phenylalanine methyl ester.

EXAMPLE 3

Isolation and characterization of N-acetoacetyl-L-aspartic anhydride 2.0 parts of sodium hydroxide were dissolved in 25 parts by volume of water and cooled to 0°–10° C. Then 3.33 parts L-aspartic acid were added and the mixture stirred until all dissolved. To this mixture was added 3.95 parts by volume of diketene dropwise while maintaining temperature and continued stirring for 3 hours. The solvent was evaporated from the homogeneous solution under vacuum at 35°–40° C. until the mixture began to foam. 25 parts by volume of acetic acid was added and evaporation was repeated. This process was repeated twice to give 20.7 parts of clear solution. To this clear solution was added 12.5 parts by volume of ethyl acetate and 4.7 parts by volume of acetic anhydride. After about 1 hour a thick precipitate formed and stirring was continued for 18 hours. The solid was isolated by filtration, washed twice with 10 parts by volume of cold ethyl acetate and dried under vacuum at 35°–40° C. for 24 hours to give 9.85 parts of anhydride contaminated with sodium acetate/acetic acid. This material was stirred with 100 parts by volume of dioxane for 5 hours. After filtration to remove remaining solid, the dioxane was evaporated under vacuum at 35°40° C. and the residue was dried under vacuum at the same temperature for 24 hours to give 1.08 parts of N-acetoacetyl-L-aspartyl anhydride, mp 131.5°–135° C:

Elemental analysis for $C_8H_9NO_5$: Calc. C, 48.25; H, 4.55; N, 7.03; Found: C, 48.42; H, 4.50; N, 6.72.

NMR (Dimethylformamide-D7): δ2.23, 3H, s; 2.8–3.7, 2H, AB portion of ABX; 3.53, 2H, s; 4.99, 1H, m; 9.04, 1H, m.

EXAMPLE 4

Preparation and isolation of N-acetoacetyl-α-L-aspartyl-L-phenylalanine methyl ester 4.5 parts of diketene were added dropwise to a stirred suspension of 14.7 parts α-L-aspartyl-L-phenylalanine methyl ester in 400 parts by volume of tetrahydrofuran and stirred for 20 hours at ambient temperatures. An additional 4.2 parts of diketene was added. After 18 hours, the solvent was removed under vacuum and the residue was purified by chromatography on silica gel to give N-acetoacetyl-α-L-aspartyl-L-phenylalanine methyl ester, mp. 118.5°–121° C. whch eluted in a 10:90:0.1 ethanol: methylene chloride:acetic acid mixture.

Elemental analysis for $C_{18}H_{22}N_2O_7$: Calc. C, 57.14; H, 5.86; N, 7.40; Found C, 56.91; H, 5.80; N, 7.31.

NMR (Dimethyl sulfoxide-D6): δ2.13, 3H, s; 2.59, 2H, m; 3.02, 2H, m; 3.35, 2H, s; 3.60, 3H, s; 4.53, 2H, m; 7.24, 5H, s: 8.30, 2H, m.

EXAMPLE 5

N-acetoacetyl-L-aspartyl anhydride 21.72 parts of N-acetoacetyl-L-aspartic acid, 0.14 parts of magnesium acetate, and 9.5 parts by volume of acetic anhydride were mixed with 200 parts by volume of ethyl acetate and heated at 55°±2° C. under argon for 24 hours.

N-acetoacetyl-L-aspartyl-L-phenylalanine methyl ester

To the above mixture was added 60 parts by volume of a 1.67M solution of L-phenylalanine methyl ester in ethyl acetate over 90 minutes. The resulting solution was stirred at ambient temperatures for 2 hours.

α-L-aspartyl-L-phenylalanine methyl ester

To the above solution was added 260 parts by volume of hexane, 336 parts by volume of water, 1.65 parts by volume of concentrated hydrochloric acid, and 6.95 parts of hydroxylamine hydrochloride. The resulting two-phase mixture was stirred at ambient temperatures for 2 hours. The aqueous layer was drawn off and treated with sodium carbonate to bring to pH 3.0. The solution was heated to 60° C. and sodium carbonate was again added to bring to pH 4.6. The solution was allowed to cool to 24° C. and was then stored at 0°–5° C. overnight. The precipitate was removed by filtration, washed with 75 parts by volume of cold water and pulled dry for 30 minutes, then dried under vacuum at 60° C. overnight to give 14.3 parts α-L-aspartyl-L-phenylalanine methyl ester.

EXAMPLE 6

N-acetoacetyl-L-aspartyl anhydride

A. 2.17 parts of N-acetoacetyl-L-aspartic acid, 1.02 parts by volume of acetic anhydride, and 0.014 parts of magnesium acetate were mixed with 40 parts by volume of ethyl acetate and heated at 55° C. under nitrogen for 24 hours. 30 parts by volume of methanol was added and the mixture stirred at ambient temperatures for 5 hours. HPLC analysis of the resulting solution showed only 0.5% unreacted N-acetoacetyl-L-aspartic acid.

B. N-acetoacetyl-L-aspartic acid, 21.7 parts, was mixed with 20 parts by volume of glacial acetic acid and 12.3 parts of acetic anhydride. Methanesulfonic acid, 0.20 parts by volume, was added to the slurry and the mixture was stirred for 100 minutes. The mixture initially thinned and then became thicker. Dry ethyl acetate, 20 parts by volume, was added and the resulting slurry was stirred for an additional 20 minutes. A solid was collected on a filter under a nitrogen atmosphere, rinsed with dry ethyl acetate, and then dried in a vacuum dessicator at 0.1 mm to afford 16.3 parts of N-acetoacetyl-L-aspartic anhydride, identified by the NMR spectrum in dimethylsulfoxide-D6.

C. N-acetoacetyl-L-aspartic acid, 21.7 parts, was mixed with 20 parts by volume of glacial acetic acid and 12.3 parts of acetic anhydride. Anhydrous magnesium acetate, 0.40 parts, was added to the slurry which thinned briefly and then thickened rapidly. After 20 minutes, the slurry was thinned by addition of 10 parts by volume of dry ethyl acetate. The resulting slurry was again thinned after an additional 15 minutes upon addition of 10 parts by volume of dry ethyl acetate. The product was collected on a filter under nitrogen after a total reaction time of 60 minutes. After the solid was rinsed with dry ethyl acetate, it was dried in a vacuum dessicator at 0.1 mm to afford 17.2 parts N-acetoacetyl-L-aspartic anhydride.

D. N-acetoacetyl-L-aspartic acid, 21.7 parts, was slurried with 20 parts by volume of dry acetone and 10.7 parts acetic anhydride. Anhydrous magnesium acetate, 0.20 parts, was dissolved in 2.0 volumes glacial acetic acid and the solution was added to the stirred slurry of N-acetoacetyl-L-aspartic acid. The mixture was stirred for 3 hours at room temperature and the solid was then collected on a filter under nitrogen. The solid was rinsed with dry ethyl acetate and then dried at 0.1 mm to afford 17.3 parts of N-acetoacetyl-L-aspartic anhydride.

E. N-acetoacetyl-L-aspartic acid, 21.7 parts, was mixed with 30 parts by volume of n-butyl acetate and 10.7 parts acetic anhydride. A solution of 0.20 parts anhydrous magnesium acetate in 2.0 parts by volume of glacial acetic acid was added and the slurry was stirred for 30 minutes at 25° C. The mixture was stirred for 2.5 hours at 40°–50° C. and then was cooled to 25° C. The solid was collected on a filter under nitrogen, it was rinsed with n-butyl acetate, and then was dried at 0.1 mm to afford 19.3 parts N-acetoacetyl-L-aspartic anhydride.

F. Substitution of 4-methyl-2-pentanone for n-butyl acetate in Example 6-E above) and with a 2 hour reaction period at 40°–50° C. afforded 18.9 parts of N-acetoacetyl-L-aspartic anhydride.

G. N-acetoacetyl-L-aspartic acid, 21.7 parts, was mixed with 25 parts by volume of 2-butanone and 10.8 parts acetic anhydride. A solution of 0.056 parts magnesium oxide in 2.0 parts by volume of glacial acetic acid was added and the mixture was stirred at room temperature for 90 minutes. The solid was collected on a filter under nitrogen, rinsed with 2-butanone, and dried at 0.1 mm to afford 17.3 parts N-aceto-acetyl-L-aspartic anhydride.

H. N-acetoacetyl-L-aspartic acid, 80.4 parts, was mixed with 111 parts by volume of dry n-propyl acetate and 39.6 parts of acetic anhydride. A solution of 0.207 parts magnesium oxide in 7.4 parts by volume glacial acetic acid was added and the mixture was stirred at 45°–50° C. for 75 minutes. The resulting slurry was cooled to 10° C. and the solid was collected on a filter under nitrogen. The solid was rinsed with n-propyl acetate and dried at 0.1 mm to afford 70.3 parts of N-acetoacetyl-L-aspartic anhydride.

I. Reaction of 22.8 parts N-acetoacetyl-L-aspartic acid with 11.25 parts acetic anhydride, 0.059 parts magnesium oxide, and 2.1 parts by volume glacial acetic acid in 32 parts by volume isopropyl acetate at 45°–50° C. for 100 minutes as described above in Example 6-H above afforded 19.5 parts N-acetoacetyl-L-aspartic anhydride.

J. 2.0 parts of magnesium acetate were dissolved in 21.0 parts of acetic acid. To the resulting solution were added 107.0 parts of acetic anhydride, 300 parts by volume of n-propyl acetate, and 217.18 parts of N-acetoacetyl-L-aspartic acid. The mixture was heated to 50° C. and reacted exothermically at 50°–58° C. for 0.5 hours. Heating was continued at 50°–52° C. for 1.0 hours. The mixture was cooled to 0°–5° C., filtered, and washed with 200 parts by volume of cold n-propyl acetate. After drying under vacuum overnight, 196.4 parts of N-acetoacetyl-L-aspartic anhydride was obtained.

EXAMPLE 7

N-acetoacetyl-L-aspartic acid

A. Potassium hydroxide (90%) 49.9 parts, was dissolved in 250 parts by volume of methanol and the resulting solution was cooled to 25° C. L-aspartic acid, 53.2 parts, was added with good stirring and the resulting solution was cooled to 0° C. with a dry ice alcohol bath. Diketene, 35.2 parts, was added over a period of about 20 minutes while maintaining the temperature within a range of from about −4° to 0° C. The solution was stirred at 0° C. for an additional 10 minutes and then was allowed to warm to 10°–15° C. Phosphoric acid (85%), 54.5 parts by volume, was added with continued stirring and cooling, the temperature being maintained at 10°–15° C. The mixture was stirred for an additional 30 minutes and then was filtered. The solid potassium dihydrogen phosphate was rinsed with about 200 parts by volume of methanol and the filtrates were combined. Methanol was distilled from the filtrate at a vacuum of 25–50 mm Hg to leave a syrup containing N-acetoacetyl-L-aspartic acid and water. Water was removed from the product by evaporation under a higher vacuum (<1 mm Hg) at about 70° C. to leave a solid residue of 84.6 parts of N-acetoacetyl-L-aspartic acid.

B. L-aspartic acid, 53.2 parts, was slurried with 120 parts by volume of water and 41.1 parts by volume of 51.6% aqueous sodium hydroxide solution was added with stirring and cooling. The resulting solution was cooled to 0°–10° C. and 20 parts by volume of 2-butanone was added. Diketene, 35.2 parts, was added during about 20 minutes while maintaining the temperature at about 10° C. The mixture was stirred at about 10° C. for an additional 10 minutes and then was allowed to warm to 15°–20° C. Additional 2-butanone, 80 parts by volume, was added and the mixture was acidified by addition of 22.2 parts by volume of concentrated sulfuric acid. The temperature of the mixture was allowed to rise to 40°–45° C. to prevent crystallization of sodium sulfate. The 2-butanone layer was separated and the aqueous layer was extracted three times with 50 parts by volume portions of 2-butanone; the mixture was maintained at a temperature of 35°–40° C. during these extractions. The combined extracts were dried over sodium sulfate, filtered, and the 2-butanone was distilled under a vacuum of 25–30 mm Hg to leave a syrup containing water and N-acetoacetyl-L-aspartic acid. Water was removed from the product by evaporation under a higher vacuum (<1 mm Hg) at about 70° C. to leave a solid residue of about 79.4 parts of N-acetoacetyl-L-aspartic acid.

C. L-aspartic acid, 133.1 parts, was slurried with 375 parts by volume of water and 81.5 parts 98.2% sodium hydroxide were added with cooling and stirring, the temperature being kept below 35° C. After all solid had dissolved, 50 parts by volume of 2-butanone were added and the mixture was cooled to −6° C. Diketene, 88 parts, was then added gradually over a period of 30–40 minutes with good stirring, with the temperature being maintained at from about −6° to −4° C. The mixture was then stirred for an additional 30–45 minutes without cooling. The pH of the reaction mixture initially was about pH 11.5 but fell to about pH 9 or less at the end of the reaction period. To the reaction mixture was then added 61 parts by volume of concentrated sulfuric acid with constant stirring but without cooling. The resulting mixture having a pH from about 1.9–2.0 was then warmed further to 40°–45° C. Additional 2-butanone, 250 parts by volume, was added and the liquid layers were well mixed. The organic layer was then separated and the aqueous layer was extracted at 40°–45° C. three times with 125 parts by volume portions of 2-butanone to which 12.5 parts by volume of water had been added. The aqueous layer was given a final extraction with 125 parts by volume of 2-butanone and the combined organic extracts were shaken with a little sodium sulfate to remove suspended water droplets. The extract was filtered and 2-butanone was distilled at 25–30 mm pressure to leave a residual solution of N-acetoacetyl-L-aspartic acid in water. The temperature of the solution was increased to 80°–90° C. in order to distill much of the water resulting in the formation of a thick syrup. The warm syrup was immediately mixed with 250 parts by volume of acetone and the mixture was stirred well. N-acetoacetyl-L-aspartic acid soon crystallized and the resulting slurry was cooled to about 10° C. The solid was collected on a funnel, rinsed with acetone, and then dried at 65° C. Acetone and some water were removed from the filtrate by distillation and the residual syrup was stirred with 70 parts by volume of acetone to afford a second crop of N-acetoacetyl-L-aspartic acid. A small third crop was obtained by reworking the filtrate from the second crop. The yield of crystalline N-acetoacetyl-L-aspartic acid in three crops averaged 193.3 parts.

D. L-aspartic acid, 133.1 parts, was slurried with 375 parts by volume of water and 81.5 parts 98.2% sodium hydroxide were added with cooling and stirring, the temperature being kept below 35° C. After all solid had dissolved, 50 parts by volume of 2-butanone were added and the mixture was cooled to −6° C. Diketene, 88 parts, was then added gradually over a period of 30-40 minutes with good stirring, with the temperature being maintained at from about −6° to −4° C. The mixture was then stirred for an additional 30-45 minutes without cooling. The pH of the reaction mixture initially was about pH 11.5 but fell to about pH 9 or less at the end of the reaction period. To the reaction mixture was then added 61 parts by volume of concentrated sulfuric acid with constant stirring but without cooling. The resulting mixture having a pH from about 1.9-2.0 was then warmed further to 40°-45° C. Additional 2-butanone, 250 parts by volume, was added and the liquid layers were well mixed. The organic layer was then separated and the aqueous layer was extracted at 40°-45° C. three times with 125 parts by volume portions of 2-butanone to which 12.5 parts by volume of water had been added. The aqueous layer was given a final extraction with 125 parts by volume of 2-butanone and the combined organic extracts were shaken with a little sodium sulfate to remove suspended water droplets. The extract was filtered and the filtrate was then placed in a flask equipped with a short Vigreux column and 2-butanone-water azeotrope was distilled while periodic additions of 2-butanone were made to the still pot. A total of 1000 parts by volume of 2-butanone were added during the distillation and about 1450 parts by volume of azeotrope were taken off at the top of the fractionating column. The boiling point measured at the top of the column gradually rose from 73.0° C. to about 78.5° C. during the distillation. N-Acetoacetyl-L-aspartic acid began to crystallize from the liquid in the still pot during the course of the distillation. When distillation was complete, the pot residue was weighed to ensure that it contained about 125 parts by volume of 2-butanone. The slurry was cooled to 5° C., whereupon more N-acetoacetyl-L-aspartic acid crystallized. The solid was collected on a filter, it was rinsed with 100 parts by volume of 2-butanone, and then was dried to constant weight. Concentration of the filtrate afforded a small second crop. The total yield of N-acetoacetyl-L-aspartic acid was about 192.4 parts.

EXAMPLE 8

Preparation of N-acetoacetyl-α,
β-aspartylphenylalanine methyl ester

A. N-acetoacetyl-L-aspartic anhydride, 10 parts, was slurried with 60 parts by volume of dry n-propyl acetate. A solution of 9.0 parts L-phenylalanine methyl ester in 15 parts by volume of n-propyl acetate was added with good stirring during 15 minutes, the temperature being maintained within a range of 25±2° C. The anhydride largely dissolved and the product began to separate. At the end of 2 hours, the reaction mixture had set up to a gelatinous mass. The material was slurried by addition of more solvent; the solvent was then distilled at 30 mm pressure to leave a solid residue. This residue was ground in a mortar and was dried at 0.1 mm to afford 18.5 parts of a mixture of the α and β isomers of N-acetoacetylaspartyl-phenylalanine methyl ester. The α:β isomer ratio was determined to be 82:18 by HPLC.

B. Similar reactions performed in ethyl acetate and n-butyl acetate afforded 18.6 and 19.2 parts respectively of a mixture of the α and β isomers of N-acetoacetylaspartylphenylalanine methyl ester; the α:β isomer ratios of the products were 83:17 and 81:19 respectively.

C. Repetition of the coupling reactions in the previous example but with addition of 11.4 parts by volume of glacial acetic acid (i.e. 4 mole equivalents) to the slurry of N-acetoacetyl-L-aspartic anhydride prior to addition of L-phenylalanine methyl ester afforded, in n-propyl acetate, ethyl acetate, and n-butyl acetate respectively, a mixture of α and β isomers of N-acetoacetyl-aspartylphenylalanine methyl ester in yields of 19.0, 19.1, and 19.1 parts respectively. The α:β isomer ratios of the products were determined by HPLC to be 82:18, 81:19, and 81:19 respectively.

EXAMPLE 10

Coupling of N-acetoacetyl-L-aspartic anhydride with L-phenylalanine methyl ester:

A. 6.40 parts of N-acetoacetyl-L-aspartic anhydride were slurried in 36 parts by volume of acetone. 55 parts by volume of an 0.581 N solution of L-phenylalanine methyl ester in toluene was evaporated to dryness under vacuum at 35°-40° C., the residue was dissolved in 9 parts by volume of acetone, and the resulting solution was added dropwise to the slurry at 25±° C. over a 14 minute period. Stirring was continued for 2 hours, at which time an aliquot was withdrawn and the ratio of α to β isomers of N-acetoacetyl-L-aspartyl-L-phenylalanine methyl ester was determined by HPLC.

B. 6.04 parts of N-acetoacetyl-L-aspartic anhydride; were dissolved in 36 parts by volume of dimethylformamide containing 6.8 parts by volume of acetic acid. Phenylalanine methyl ester, from 51 parts by volume of an 0.581N solution in toluene, in 9 parts by volume of dimethylformamide was added over a 15 minute period at a temperature of 25±2° C. and stirring was continued for 2 hours. An aliquot was withdrawn and the isomer ratio determined by HPLC.

C. 6.35 parts of N-acetoacetyl-L-aspartic anhydride in 36 parts of carbon tetrachloride were treated with phenylalanine methyl ester, from 55 parts by volume of an 0.581N solution in toluene, in 9 parts by volume of carbon tetrachloride as in the previous example. The resulting gel was dissolved in aqueous acetonitrile and the two phase solution was evaporated to dryness under vacuum. The residue was dissolved in aqueous acetonitrile, an aliquot was withdrawn and the isomer ratio determined by HPLC.

D. In accordance with the above procedures, the coupling of N-acetoacetyl-L-aspartic anhydride with L-phenylalanine methyl ester was conducted using the solvents listed in Table I. The α:β APM ratios obtained with and without the addition of acetic acid to the N-acetoacetyl-L-aspartic anhydride prior to coupling with phenylalanine methyl ester are illustrated in Table I.

TABLE I

| Solvent | α:β Ratio Without Acetic Acid | α:β Ratio with Acetic Acid |
|---|---|---|
| Ethyl Carbonate | 76:24 | 83:17 |
| Ethylene Carbonate | 61:39 | 69:31 |
| Butyrolactone | 62:38 | 71:29 |
| Acetone | 74:26 | 76:24 |
| 2-Butanone | 76:24 | 77:23 |
| 4-Methyl-2-Pentanone | 78:22 | 78:22 |
| t-Butyl Alcohol | 64:36 | 75:25 |
| Methyl-t-Butyl Ether | 56:44 | 80:20 |
| Tetrahydrofuran | 77:23 | 80:20 |
| Dioxane | 78:22 | 82:18 |
| Dimethoxyethane | 76:24 | 78:22 |

TABLE I-continued

| Solvent | α:β Ratio Without Acetic Acid | α:β Ratio with Acetic Acid |
| --- | --- | --- |
| Cyclohexane | 64:36 | 74:26 |
| Toluene | 54:46 | 79:21 |
| Chlorobenzene | 58:42 | 77:23 |
| Methylene Chloride | 79:21 | 78:22 |
| Chloroform | 75:25 | 79:21 |
| Carbon Tetrachloride | 50:50 | 77:23 |
| Ethylene Dichloride | 76:24 | 77:23 |
| Acetonitrile | 74:26 | 76:24 |
| Pyridine | 55:45 | — |
| Dimethyl Formamide | 27:73 | 58:42 |
| Dimethyl Sulfoxide | 20:80 | 29:71 |
| Tetramethylene Sulfone | 54:46 | 69:31 |

EXAMPLE 12

L-aspartyl-L-phenylalanine methyl ester hydrochloride dihydrate 0.2 parts of magnesium acetate were dissolved in 11.4 parts by volume of acetic acid. To this solution was added 9.9 parts by volume of acetic anhydride, 120 parts by volume of toluene, and 21.72 parts of N-acetoacetylaspartic acid. The resulting mixture was heated at 50° C. under nitrogen for 1.5 hours, then cooled to 20°–25° C. A solution containing 17.92 parts L-phenylalanine methyl ester in 30 parts by volume of toluene was added dropwise over a 20 minute period and the mixture stirred overnight. 6.95 parts of hydroxylamine hydrochloride in 100 parts by volume of water was added and stirring was continued for 2.5 hours. The aqueous layer was separated, extracted four times with 50 parts by volume of methylene chloride and cooled to 5° C. 15 parts by volume of concentrated hydrochloric acid were added and the mixture stirred at 5° C. for 1.5 hours. The precipitate was collected on a filter and pulled dry overnight to give 25.93 parts of L-aspartyl-L-phenylalanine methyl ester hydrochloride dihydrate.

EXAMPLE 13

Variation of α/β Coupling Ratio as a Function of Temperature 5.99 parts N-acetoacetyl-L-aspartic anhydride was slurried with 36 parts by volume n-propyl acetate. Optionally, 7.2 parts of acetic acid was added at this point and the mixture was cooled or heated to the required temperature. A solution of 5.39 parts L-phenylalanine methyl ester in 9 parts by volume n-propyl acetate was added dropwise over 15 minutes and the temperature was maintained for an additional 2 hours. The resulting gelatinous mixture was dissolved in aqueous acetonitrile and evaporated to dryness under vacuum. The residue was analyzed by HPLC for α and β-N-acetoacetyl-L-aspartyl-L-phenylalanine methyl ester. The α:β ratios obtained with and without addition of acetic acid to the N-acetoacetyl-L-aspartic anhydride prior to coupling with phenylalanine methyl ester are illustrated in Table II.

TABLE II

| Solvent | α:β Ratio Without Acetic Acid | α:β Ratio with Acetic Acid |
| --- | --- | --- |
| 0–5° C. | 73:27 | 80:20 |
| 15° C. | 69:31 | |
| 25° C. | 79:21 | 82:18 |
| 35° C. | 80:20 | |
| 50° C. | 75:25 | 77:23 |

EXAMPLE 14

Conversion of N-Acetoacetyl-α-L-Aspartyl-L-Phenylalanine Methyl Ester to α-L-Aspartyl-L-Phenylalanine Methyl Ester Using Hydrazine Salt Dihydrochloride N-Acetoacetyl-α-L-Aspartyl-L-phenylalanine methyl ester, 4.29 parts, was mixed with 52 parts by volume of water and 1.19 parts of hydrazine dihydrochloride at room temperature and the mixture was stirred. Most of the solid was dissolved after 40 minutes and solution was complete after 75 minutes. Stirring was continued for a total reaction time of 175 minutes. An aliquot of the solution (pH about 1.2) was adjusted to pH 4.5 by addition of sodium acetate and then was assayed for α-L-aspartyl-L-phenylalanine methyl ester by HPLC. The reaction mixture was found to contain 3.09 parts of α-L-aspartyl-L-phenylalanine methyl ester.

What is claimed is:

1. A chemical reaction mixture for preparing α-L-aspartyl-L-phenylalanine methyl ester containing a compound of the class consisting of N-acetoacetyl-L-aspartic acid, N-acetoacetyl-L-aspartic anhydride and N-acetoacetyl-α-L-aspartyl-L-phenylalanine.

2. A chemical reaction mixture according to claim 1 containing N-acetoacetyl-L-aspartic acid and N-acetoacetyl-L-aspartic anhydride.

* * * * *